US009254185B2

(12) United States Patent
Vila

(10) Patent No.: US 9,254,185 B2
(45) Date of Patent: Feb. 9, 2016

(54) REPLACEABLE HEAD AND IMAGE CAPTURING TOOTHBRUSH

(71) Applicant: Luis Vila, Greer, SC (US)

(72) Inventor: Luis Vila, Greer, SC (US)

(*) Notice: Subject to any disclaimer, the term of this patent is extended or adjusted under 35 U.S.C. 154(b) by 186 days.

(21) Appl. No.: 14/183,628

(22) Filed: Feb. 19, 2014

(65) Prior Publication Data

US 2015/0230595 A1 Aug. 20, 2015

(51) Int. Cl.
| A46B 13/02 | (2006.01) |
| A46B 15/00 | (2006.01) |
| A61C 17/26 | (2006.01) |
| A61C 17/22 | (2006.01) |
| A61C 9/00 | (2006.01) |

(52) U.S. Cl.
CPC ............... *A61C 17/26* (2013.01); *A46B 15/002* (2013.01); *A46B 15/0004* (2013.01); *A61C 9/004* (2013.01); *A61C 9/0053* (2013.01); *A61C 17/22* (2013.01); *A61C 17/221* (2013.01); *A61C 17/224* (2013.01); *A46B 13/02* (2013.01); *A46B 15/0036* (2013.01)

(58) Field of Classification Search
CPC .... A46B 13/02; A46B 15/00; A46B 15/0002; A46B 15/0004; A61C 17/22; A61C 17/221; A61C 17/24; A61C 17/26; A61C 17/224; A61C 17/32; A61C 17/34
USPC ..................................................... 15/22.1, 28
See application file for complete search history.

(56) References Cited

U.S. PATENT DOCUMENTS

| 2,140,307 | A | * | 12/1938 | Belaschk | ............... | A61C 17/26 15/180 |
| 3,242,516 | A | * | 3/1966 | Cantor | ................... | A61C 17/26 15/28 |
| 2009/0056044 | A1 | * | 3/2009 | Rizoiu | .................. | A46B 5/002 15/22.1 |
| 2010/0281636 | A1 | * | 11/2010 | Ortins | ...................... | A46B 9/04 15/4 |
| 2010/0309302 | A1 | * | 12/2010 | Yang | .................. | A61B 1/00016 348/77 |
| 2012/0036658 | A1 | * | 2/2012 | Schaefer | .............. | A61C 17/222 15/28 |
| 2012/0192367 | A1 | * | 8/2012 | Lin | ...................... | A61C 17/224 15/22.1 |
| 2013/0061412 | A1 | * | 3/2013 | Vashi | ................... | A46B 5/0095 15/106 |
| 2015/0107034 | A1 | * | 4/2015 | Shani | .................. | A61C 17/221 15/22.1 |

* cited by examiner

*Primary Examiner* — Mark Spisich
(74) *Attorney, Agent, or Firm* — Ruben Alcoba, Esq.

(57) ABSTRACT

A dual purpose toothbrush that allows a user to clean his or her teeth and that also serves the purpose of preserving the record of the user's mouth via stored digital images. The dual purpose toothbrush that has a replaceable cartridge of rotating bristles and a camera system on the head of the toothbrush, a camera board that operates the basic functions of the camera and the rotating bristles of the toothbrush while temporarily storing images taken by the camera, a plurality of inputs that allow a user to operate the toothbrush, a wiring system that connects the components of the toothbrush, a rechargeable battery, and a port for charging and downloading images to a peripheral device.

4 Claims, 3 Drawing Sheets

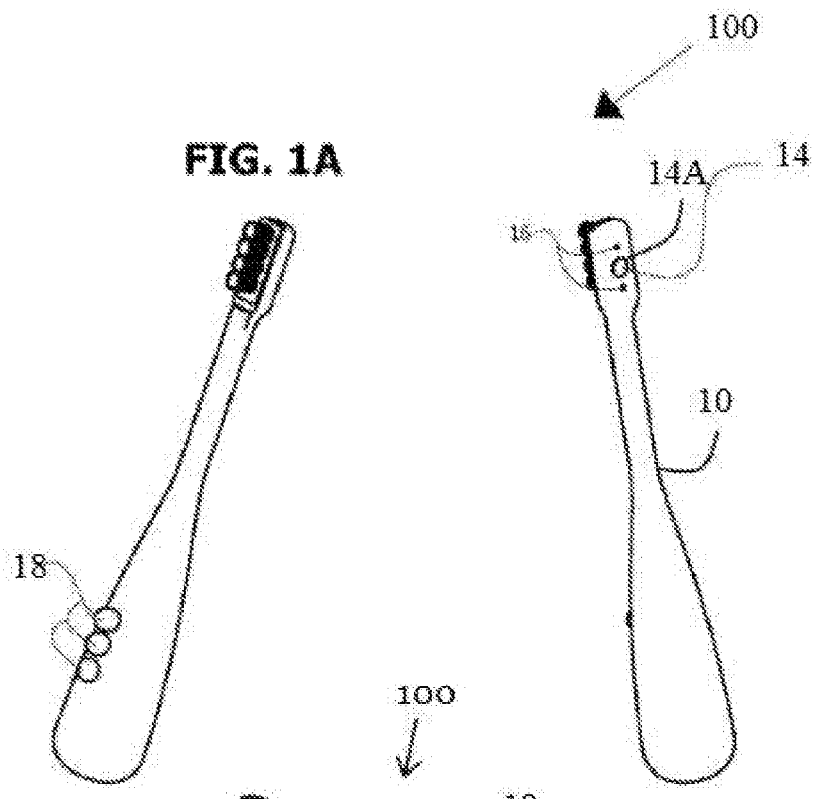
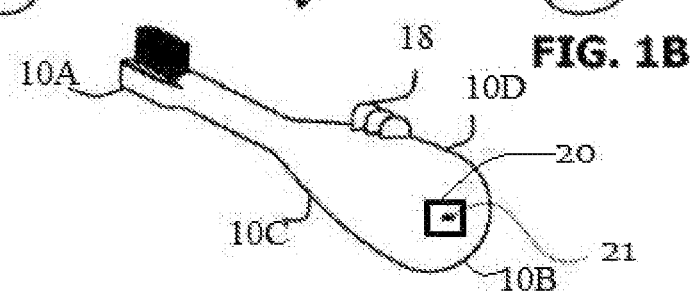

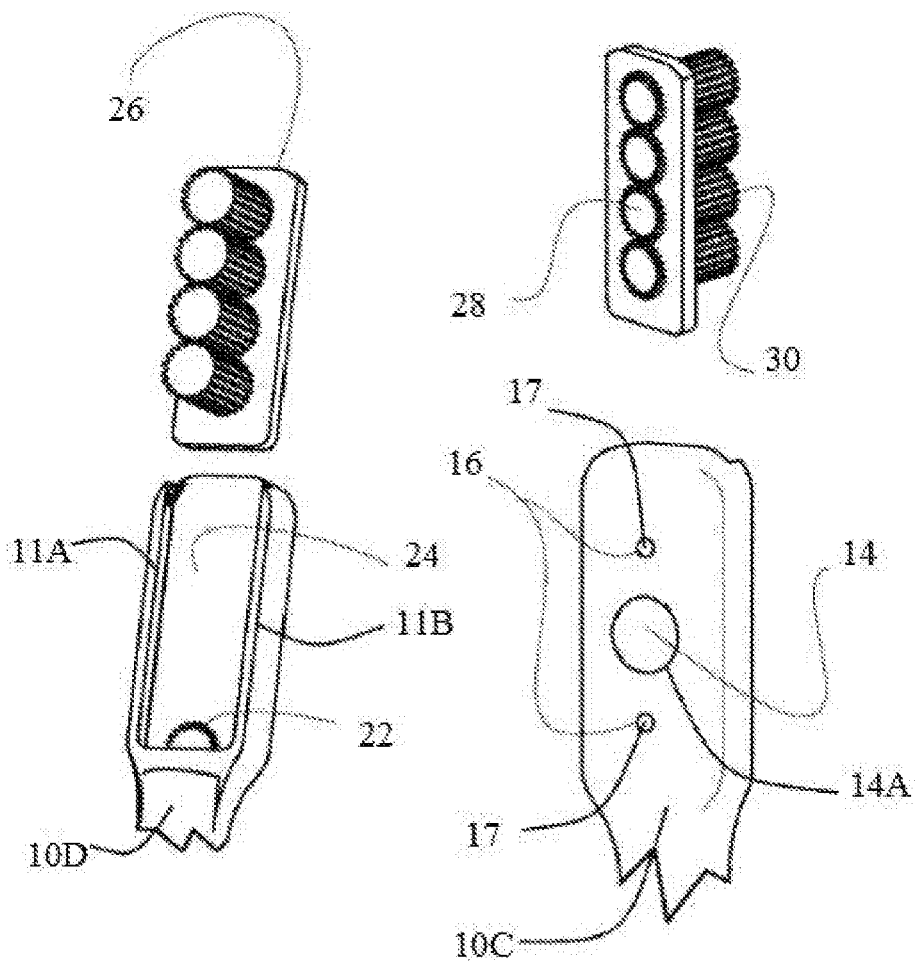

REPLACEABLE HEAD AND IMAGE CAPTURING TOOTHBRUSH

BACKGROUND

The present invention relates generally to toothbrushes, and, more particularly, to a powered toothbrush having a head with a plurality of movably mounted bristle sections that also comprises of an imaging capturing and storing system that can be later downloaded into a computer or any other similar analyzing device or system.

For ages man has blown the importance of maintaining good oral hygiene. The result of not maintaining good oral hygiene is at best the loss of ones teeth and at worst the start of other immunological diseases that are caused by the decay of the teeth and gums of a human.

The history of recorded oral hygiene has shown how man has evolved from using sticks to clean one's teeth to the present state of the art of using powered toothbrushes to accomplish the same.

The inventor of the present invention has developed a toothbrush that will capture digital images of the user's mouth that also has the dual use of being a rotary toothbrush. The placement of a digital camera in the toothbrush provides the user with one standalone device that allows for the maintenance of one's teeth while preserving the record of the user's mouth over time.

The capturing of the digital images of the user's mouth allows the user to preserve a record of the user's mouth, while also allowing the user to have a record of his or her dental hygiene that can be delivered to a dental professional. This is a key aspect of the present invention.

In the art of powered toothbrushes there are presently many different variation of powered toothbrushes. For example, U.S. Pat. No. 5,416,942, discloses a motorized anti-plaque toothbrush that comprises a handle at one end of which is a cleaning/massaging head, in particular a brushing head, which rotates about an axis winch is approximately perpendicular to the longitudinal axis of the handle and is turned with a continuous one-way rotary motion or with a reciprocating rotary motion by a motor, preferably an electric motor, housed in the handle. According to the invention, the cleaning/massaging head is composed of at least two separate cleaning/massaging tool parts that are supported coaxially with respect to each other in such a way that they can rotate relative to each other, being turned in mutually opposite directions in the case of continuous one-way rotation and in phase opposition to each other in the case of reciprocating rotation. The "942" patent does not disclose a toothbrush that has a replaceable cartridge of rotary bristle tufts that also captures digital images of the user's mouth.

The replaceable cartridge of rotary bristle tufts is another key aspect of the present invention, for the ease of replacement of the cartridge encourages its users to replace the cartridges periodically, thereby limiting the bacteria that can develop over the bristles over time. The replaceable cartridge also allows the user of the toothbrush to have a dual purpose device that does not have to discarded over time because of the buildup of bacteria over the bristles of the toothbrush.

For the foregoing reasons there is a need for a dual purpose toothbrush that will allow a user to clean ins or her teeth and that will also serve the purpose of preserving the record of the user's mouth via stored digital images.

SUMMARY

The present invention is directed to a dual purpose toothbrush that allows a user to clears his or her teeth and that also serves the purpose of preserving the record of the user's mouth via stored digital images.

The present invention is a dual purpose toothbrush that has a replaceable cartridge of rotating bristles and a camera system on the head of the toothbrush, a camera board that operates the basic functions of the camera and the rotating bristles of the toothbrush while temporarily storing images taken by the camera, a plurality of inputs that allow a user to operate the toothbrush, a fiber optic wiring system, a rechargeable battery, and a port for charging and downloading images to a peripheral device.

An object of the present invention is to provide a device that can be used for the maintenance of a user's teeth.

Another object of the present invention is to provide a device that will allow a toothbrush to be reusable for extended periods of time.

Yet another object of the present invention is to provide the user with a toothbrush that uses a disposable bristle cartridge.

Still another object of the present invention is to provide a toothbrush that serves as an oral personal digital imaging recording device.

Yet still another object of the prevent invention is to provide an oral personal device that can help a dental professional see the history of a patients mouth via digital images captured by the device.

DRAWINGS

With the above and other related objects in view, the invention consists in the details of construction and combination of parts as will be more fully understood from the following description, when read in conjunction with the accompanying drawings in which:

FIG. 1A shows a perspective view of a powered toothbrush that shows the rotating bristles of the present invention and its control/input buttons;

FIG. 1B shows a perspective view of the present invention wherein the lens and the LED light sources are shown on the head of the toothbrush;

FIG. 1C shows a perspective view of the present invention showing its USB port, its control/input buttons, and the rotating bristles;

FIG. 2A shows a perspective view of the head of the toothbrush wherein the bristle brush cartridge is aligned above the rails of the toothbrush in which it inserts;

FIG. 2B shows a perspective view of the head of the toothbrush wherein the gears of the bristle brush cartridge are shown above the head of the toothbrush and the lens and LED lights of the head of the toothbrush are shown.

DESCRIPTION

Figure 3:
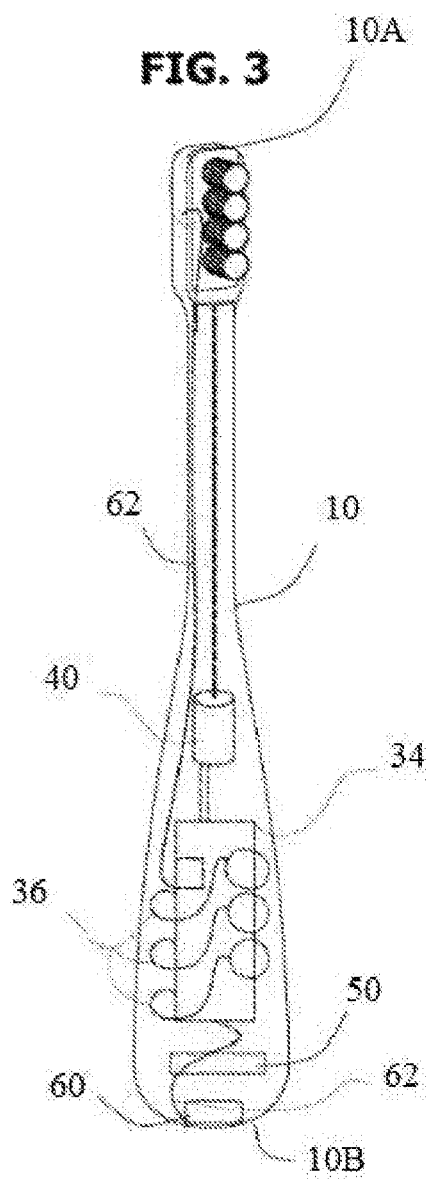
FIG. 3 shows a perspective of one embodiment of the present invention showing how some of the components of the present invention may be displaced within its housing.

As seen in FIGS. 1-3, an embodiment of the present invention discloses a powered toothbrush 100, the toothbrush 100 comprising a housing 10 having a first 10a and a second end 10b and a top 10c and a bottom 10d, the first end 10a of the housing 10 having a smaller diameter than the second end 10b, the second end 10b of the housing defining an USB aperture 20, a USB port 21 is mounted to the housing within the USB aperture 20, the bottom of the second end 10b defining at least one input aperture 36 that runs along the length of the housing 10, at least one input button 18 mounted on the housing 10 within each input aperture 36, the top of the first end 10a of the housing 10 defining a pair of LED apertures 16 and a lens aperture 14 centered between the LED apertures 16, a pair of LED lights 17 are mounted on the housing 10 at the LED apertures 16 and a lens 14 that is mounted on the housing 10 within the lens aperture 14a, the bottom of the first end 10a defining a left 11a and a right rail 11b that run along the length of the housing 10, the left 11a and right rail 11b define a cartridge insert port 24. The toothbrush 100 further comprises of a drive gear 22 attached to the housing 10 at a position that is centered between the left 11a and the right rail 11b, the drive gear 22 is connected to a motor 40. The toothbrush 100 further comprises of a bristle brush cartridge 26 that has a plurality of drive brush gears 28 and a plurality of rotating bristles 30, the bristle brush cartridge 26 is inserted within the left 11a and right rail 11b of the housing 10 so that the one of the drive brush gears 28 is flush with the drive gear 22. The toothbrush 100 further comprises of a control board 34 that houses a plurality of components that allow the toothbrush 100 to capture and save images taken by the toothbrush 100 and that control the mechanical functions of the toothbrush 100. The toothbrush 100 further comprises of a rechargeable battery 50 that powers the toothbrush 100. And lastly, the toothbrush 100 further comprises of a plurality of wires (not shown in figures) that connect the LED lights 17, the lens 14, the input buttons 18, the rechargeable battery 50, and the USB port 60 to the control board 34.

In an embodiment of the present invention, the lens 14 of the powered toothbrush 100 is connected to the control board 34 via a fiber optic wire 62.

In another embodiment of the present invention, the USB port 60 of the powered toothbrush 100 is connected to the control board 34 via a fiber optic wire.

In still another embodiment of the present invention, the drive brush gears 28 of the bristle brush cartridge 26 of the powered toothbrush 100 are serially connected so that each drive brush gear 28 spins in an opposite direction to its adjacent drive brush gear 28.

An advantage of the present invention is that it provides a device that can be used for the maintenance of a user's teeth.

Another advantage of the present invention is that it provides a device that allows a toothbrush to be reusable for extended periods of time.

Yet another advantage of the present invention is that it provides the user with a toothbrush that uses a disposable bristle cartridge.

Still another advantage of the present invention is that it provides a toothbrush that serves as a personal digital imaging recording device.

Yet still another advantage of the prevent invention is that it provides an oral personal device that helps a dental professional see the history of a patients mouth via digital images captured by the device.

Although the present invention has been described in considerable detail in reference to preferred versions, other versions are possible. Therefore, the spirit and scope of the appended claims should not be limited to the description of the preferred versions contained herein.

What is claimed is:

1. A powered toothbrush, the toothbrush comprising:
   a housing having a first and a second end and a top and a bottom, the first end of the housing having a smaller diameter than the second end, the second end of the housing defining an USB aperture, a USB port is mounted to the housing within the USB aperture, the bottom of the second end defining at least one input aperture that runs along the length of the housing, at least one input button mounted on the housing within each input aperture, the top of the first end of the housing defining a pair of LED apertures and a lens aperture centered between the LED apertures, a pair of LED lights are mounted on the housing at the LED apertures and a lens that is mounted on the housing within the lens aperture, the bottom of the first end defining a left and a right rail that run along the length of the housing, the left and right rail define a cartridge insert port;
   a drive gear attached to the housing at a position that is centered between the left and the right rail, the drive gear is connected to a motor;
   a bristle brush cartridge that has a plurality of drive brush gears and a plurality of rotating bristles, the bristle brush cartridge is inserted within the left and right rail of the housing so that the one of drive brush gears is flush with the drive gear;
   a control board that houses a plurality of components that allow the toothbrush to capture and save images taken by the toothbrush and that control the mechanical functions of the toothbrush; and
   a rechargeable battery that powers the toothbrush.

2. The powered toothbrush of claim 1, wherein the lens is connected to the control board via a fiber optic wire.

3. The powered toothbrush of claim 2, wherein the USB port is connected to the control board via a fiber optic wire.

4. The powered toothbrush of claim 3, wherein the drive brush gears of the bristle brush cartridge are serially connected so that each drive brush gear spins in an opposite direction to its adjacent drive brush gear.

* * * * *